(12) United States Patent
Kanter (10) Patent No.: US 12,169,927 B2
(45) Date of Patent: Dec. 17, 2024

(54) SYSTEM AND A METHOD FOR ALERTING ON VISION IMPAIRMENT

(71) Applicant: SHAMIR OPTICAL INDUSTRY LTD., Kibbutz Shamir (IL)

(72) Inventor: Amnon Kanter, Kibbutz Lehavot HaBashan (IL)

(73) Assignee: SHAMIR OPTICAL INDUSTRY LTD., Kibbutz Shamir (IL)

( * ) Notice: Subject to any disclaimer, the term of this patent is extended or adjusted under 35 U.S.C. 154(b) by 516 days.

(21) Appl. No.: 17/310,852

(22) PCT Filed: Feb. 27, 2020

(86) PCT No.: PCT/IL2020/050222
§ 371 (c)(1),
(2) Date: Aug. 26, 2021

(87) PCT Pub. No.: WO2020/174475
PCT Pub. Date: Sep. 3, 2020

(65) Prior Publication Data
US 2022/0189010 A1    Jun. 16, 2022

Related U.S. Application Data

(60) Provisional application No. 62/810,962, filed on Feb. 27, 2019.

(51) Int. Cl.
*A61B 3/08* (2006.01)
*A61B 3/113* (2006.01)
(Continued)

(52) U.S. Cl.
CPC ............ *G06T 7/0012* (2013.01); *A61B 3/085* (2013.01); *A61B 3/113* (2013.01); *A61B 3/1176* (2013.01);
(Continued)

(58) Field of Classification Search
USPC .............. 382/100–117, 154–224; 706/1–62, 706/900–903
See application file for complete search history.

(56) References Cited

U.S. PATENT DOCUMENTS 10,371,946 B2 * 8/2019 Samec ................. A61B 3/1015
2010/0016754 A1   1/2010 Whillock et al.
(Continued)

FOREIGN PATENT DOCUMENTS

EP      3029511      *  6/2016  ............. G02C 13/00
EP      3239870 A1     11/2017

OTHER PUBLICATIONS

Nie Weiran; Eye Condition Determination System; 2016 (Year: 2016).*

*Primary Examiner* — Marcellus J Augustin
(74) *Attorney, Agent, or Firm* — FISHERBROYLES, LLP; Roger L. Browdy; James E. Mrose (57) ABSTRACT

The present invention discloses a technique for alerting on vision impairment. The system comprises a processing unit configured and operable for receiving scene data being indicative of a scene of at least one consumer in an environment, identifying in the scene data a certain consumer, identifying an event being indicative of a behavioral compensation for vision impairment, and, upon identification of such an event, sending a notification relating to the vision impairment.

13 Claims, 3 Drawing Sheets

(51) Int. Cl.
  *A61B 3/117* (2006.01)
  *A61B 5/00* (2006.01)
  *G02B 27/00* (2006.01)
  *G06Q 30/0251* (2023.01)
  *G06T 7/00* (2017.01)
  *G06T 7/292* (2017.01)
  *G06T 7/70* (2017.01)
  *G06V 40/20* (2022.01)
  *G06V 40/16* (2022.01)

(52) U.S. Cl.
  CPC .............. *A61B 5/0022* (2013.01); *A61B 5/74* (2013.01); *G02B 27/0093* (2013.01); *G06Q 30/0251* (2013.01); *G06T 7/292* (2017.01); *G06T 7/70* (2017.01); *G06V 40/20* (2022.01); *G06T 2207/20076* (2013.01); *G06T 2207/30041* (2013.01); *G06T 2207/30201* (2013.01); *G06V 40/172* (2022.01)

(56) References Cited

U.S. PATENT DOCUMENTS

| | | | |
|---|---|---|---|
| 2013/0132898 A1* | 5/2013 | Cuento | G02C 7/027 715/810 |
| 2017/0000331 A1 | 1/2017 | Samec et al. | |
| 2019/0272726 A1* | 9/2019 | Kaib | G08B 21/18 |

\* cited by examiner

SYSTEM AND A METHOD FOR ALERTING ON VISION IMPAIRMENT

TECHNOLOGICAL FIELD

The invention relates generally to identification and recognition of an individual. More particularly, one aspect of the invention is directed to monitoring and characterization of an individual in an image.

BACKGROUND

Maintaining health is a very important aspect of human life. In today's world, the availability of sophisticated technologies and compounding scientific advancements has raised the public's expectations of what the standard of health care should be. Individuals need a means by which they can become more active and effective in the management of their health. Among other things, individuals need to be able to assess their health and understand what is normal and what is abnormal, relative to their own unique characteristics which include age, gender, physical characteristics, race, ethnicity, geographical region and so on. Also, individuals need simple and quick access to personalized health strategies that address behavioral modifications, environment optimization, nutritional optimization, physical fitness, early detection of abnormalities and disease prevention tactics that are tailored to each individual's unique characteristics and situation. There is the need to evaluate and diagnose a condition and gage the progression of a condition and the effectiveness of a health strategy or medical treatment.

GENERAL DESCRIPTION

A vision test is not commonplace in most people's daily routine. Additionally, individuals are not always aware of a decline in their visual acuity and will often compensate such a decline with certain visual habits. It is not uncommon that eyeglasses wearers are unaware that the corrective eyewear they are using does not optimally meet their visual needs. Their visual needs may be that their eye prescription (Rx) is incorrect, and they are under or over corrected, or that they are wearing eyewear that is not optimally suited to their visual behavior. For example, a lens design is uncomfortable for the user, or a lens size is too small for the user's visual needs. This is due to the ability of humans to adapt and compensate for vision impairment. However, adapting in this manner is less than optimal and can cause other problems including poor vision, eye strain, fatigue, dizziness, etc. There is a need for a technique evaluating and diagnosing vision problems, even when patients are unaware that they require the evaluation.

The present invention relates to new systems, computer program software products and new processes of fitting, buying, selling, and marketing optical related products and services. In some embodiments, a computer hardware and software combination is employed to help both optical customers and product and service providers. According to a broad aspect of the present invention, there is provided a system for alerting on vision impairment. The system comprises a processing unit configured and operable for receiving scene data being indicative of a scene of at least one consumer in an environment, identifying in the scene data a certain consumer, identifying an event being indicative of a behavioral compensation for vision impairment, and, upon identification of such an event, sending a notification relating to the vision impairment. The processing unit may be placed in the environment (e.g. being integrated in any desired devices) or, alternatively, the computer-implemented steps of receiving the scene data and/or identifying in the scene data a certain consumer, identifying an event being indicative of a behavioral compensation for vision impairment, and, upon identification of such an event, sending a notification may be performed by a server not located in the proximity of the environment. The server is in data communication with the different parts of the system. Therefore, in some embodiments of the present invention, the system of the present invention may be implemented in any personal mobile phone/tablet and may be integrated as part of e-commerce website. For example, the processing unit may send a notification to a consumer entering a website, requesting his permission to use his camera for better service/for health issues. Upon receiving scene data being indicative of a scene of at least one consumer in an environment, identifying in the scene data a certain consumer, identifying an event being indicative of a behavioral compensation for vision impairment, and, upon detection of such visual impermeant, suggesting the consumer to buy a prescription eyewear according to the identified event.

In some embodiments, the event may comprise the position and orientation of the head (i.e. face and neck), increase or decrease of viewing distance between the consumer and viewed object, and changing the position of the eyeglasses worn by the consumer. In a specific and non-limiting example, the position and orientation of the head may include at least one of squinting or chin lifting. The event may be identified by identifying images having an image feature being indicative of behavioral compensation, performing a Bruckner test, performing a Hirschberg test, and measuring the blink count/frequency. The image feature may comprise squinting, head orientation, certain distances between an object and consumer's eyes, certain position of the eyeglasses on the consumer's face, strabismus, cataracts, and reflections from the eye.

The present invention provides a technique for alerting an individual, for example while being in the proximity of retail stores, that their vision might be impaired. A vision test can then be performed or scheduled for promoting sale if a new prescription is need. The technique therefore provides improved eye care capabilities, and an increase in awareness of behavioral compensation for low visual acuity for an eye care professional and/or a consumer.

In some embodiments, the system comprises at least one sensing unit configured and operable for detecting the scene data. The sensing unit may comprise at least one imaging unit configured and operable for capturing at least one image of at least a portion of a consumer's body, at least one motion detector configured and operable for detecting consumer data being indicative of a motion of a consumer, and at least one eye tracker configured and operable for tracking eye motion of a consumer. The imaging unit may comprise a plurality of cameras placed at different heights. In a specific and non limiting example, the sensing unit may be accommodated in an optical or digital eyewear frame display.

In some embodiments, the processing unit is configured and operable for identifying a consumer's condition. The consumer's condition may comprise consumer data being indicative of the consumer's position and location relative to at least one object in the consumer's environment. Additionally or alternatively, the consumer data may also comprise at least one of a consumer's face, eyewear, posture, sound, motion, previous eyewear data information or previous eyewear preference(s).

In some embodiments, the system relates to an in-store (e.g. counter/shelf) computer-based system for making ophthalmic recommendations relating to eyewear, including recommending random consumers to have an eye check (prescription test/screening). Alternatively, the system may alert upon detecting an event indicative of unintended use of a lens design, or wrong eyewear usage, and recommend a lens design better suited to the user. The processing unit is thus configured and operable to detect a consumer, identify visual behavior (difficulties) or wrong eyewear usage behavior of the detected consumer based on recorded data, and to send an alert to the identified consumer or a third party (e.g. sellers) to approach the consumer in order to recommend a vision test, or to renew their prescription. The consumer can get a message to his personal device (e.g. mobile phone or smart watch) recommending him to take a vision test. Other eye abnormalities may also be detected in the passive observation of the consumer.

The method of vision test screening may be based on face recognition and/or pupil or gaze tracking and/or position and orientation of the head. The system of the present invention may be placed in kiosks, integrated in Virtual Try-On (VTO)s, E-COM tools or store surveillance, displays/showcases.

In some embodiments, the system comprises a camera recording at least one image of at least one consumer. The information of the consumer can be saved and cataloged in order to approach the customer whenever it is convenient for the store employee. The consumer information as used herein may refer to, but is not limited to, consumer behavior information and/or consumer profile information. The alert can be sent to a computer platform comprising the store management software or other any suitable hardware infrastructure (e.g. mobile phone or any other digital device).

The system may also be adapted for non-retail environments. For example, a medical clinic may install the system in order to passively observe patients who may be in the clinic for any medical appointment. The clinic may alert the patient to detected eye abnormality, and refer the patient to the relevant health care practitioner, e.g. eye doctor or eye M.D, ophthalmologist, optometrist or OD, or the relevant Eye Care Practitioner (ECP), thus increasing the opportunity for improvement of vision of patients who may be unaware of their vision impairments.

The notification relating to the vision impairment may include at least one of the identified event, consumer data indicative of the identified consumer, ophthalmologic recommendations based on the identified event, or lack of events, or an appointment for a vision test.

In some embodiments, the processing unit comprises a memory for storing at least one of a reference data indicative of behavioral compensation for vision impairment, data indicative of the notification, or data indicative of a follow-up of the notification. The processing unit may thus be configured for at least one of identifying the event upon comparison between the detected data and the reference data or determining a probability for a vision impairment of the consumer based on the comparison. The processing unit may comprise a communication interface being configured for sending the notification to at least one of the identified consumer or a third party.

In some embodiments, the processing unit is configured for providing a frame recommendation.

In some embodiments, the memory is configured for storing a database including a multiplicity of data sets related to a plurality of spectacle frame models and sizes.

In some embodiments, the processing unit is configured and operable to correlate between frames parameters and ophthalmic prescriptions and/or to correlate between frames parameters and facial features and/or to correlate between frames parameters and eyewear preferences.

In some embodiments, the system comprises a server and at least one computer entity linked to the server via a network, wherein the network is configured to receive and respond to requests sent across the network; transmitting one or more modules of computer executable program instructions and displayable data to the network connected user computer platform in response to a request, wherein the modules include modules configured to: receive and transmit image information, transmitting a frame recommendation and an optical lens option recommendation based on received image information, for display by the network connected user computer platform.

According to another broad aspect of the present invention, there is provided a method for alerting on vision impairment. The method comprises identifying, a certain individual (e.g. consumer) in scene data of at least one consumer in an environment; identifying an event being indicative of a behavioral compensation for vision impairment; and upon identification of such an event, sending a notification on the vision impairment.

In some embodiments, the method further comprises detecting scene data in a retail environment. Such detection may comprise at least one of capturing at least one image of at least one consumer, detecting consumer data being indicative of a motion of a consumer, or tracking an eye motion of a consumer. Capturing at least one image of at least one consumer may comprise continuously recording a scene.

In some embodiments, the method further comprises identifying in the consumer data, the consumer's condition. The consumer's condition includes data being indicative of the consumer's position and location relative to the consumer's environment.

In some embodiments, the identification of the event comprises identifying images having an image feature being indicative of behavioral compensation, performing a Bruckner test, performing a Hirschberg test, and measuring the blink count/frequency.

In some embodiments, the identification in the at least one image of a consumer in a retail environment comprises at least one of receiving data characterizing the retail environment or performing face recognition.

In some embodiments, sending a notification relating to the vision impairment comprises sending the notification to at least one of the identified consumer or a third party.

In some embodiments, the method further comprises storing at least one of a reference data indicative of behavioral compensation for vision impairment, data indicative of the notification, or data indicative of a follow-up of the notification.

In some embodiments, the method further comprises identifying the event upon comparison between the detected data and the reference data and determining a probability for a vision impairment of the consumer, based on the comparison.

According to another broad aspect of the present invention, there is provided a method for providing a frame recommendation to a consumer being based on a plurality of parameters.

According to another broad aspect of the present invention, there is provided a computer program instructions stored in the local storage that, when executed by a processing unit, cause the processing unit to: receive data being indicative of a scene of at least one consumer in an environment, identify in the data a certain consumer, identify an event being indicative of a behavioral compensation for vision impairment, and, upon identification of such an event, send a notification relating to the vision impairment.

According to another broad aspect of the present invention, there is provided a computer program product stored on a tangible computer readable medium, comprising: a library of software modules which cause a computer executing them to prompt for information pertinent to at least one of an eyeglasses recommendation and an optical lens option recommendation, to store the information or to display eyewear recommendations.

In some embodiments, the library further comprises a module for frame selection, point of sales and advertising.

According to another broad aspect of the present invention, there is provided a computer platform for facilitating eye glasses marketing or selection, comprising: a camera; a processor configured to execute computer program instructions to cause the processor to take an image of a consumer, identify in the image a certain consumer, identify an event being indicative of a behavioral compensation for vision impairment, and, upon identification of such an event, sending a notification relating to the vision impairment; local storage for processor executable instructions for carrying out storage of information.

According to another broad aspect of the present invention, there is provided a computer program intended to be stored in a memory of a processor unit of a computer system, or in a removable memory medium adapted to cooperate with a reader of the processor unit, comprising instructions for implementing the method as described above.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

Figure 1:
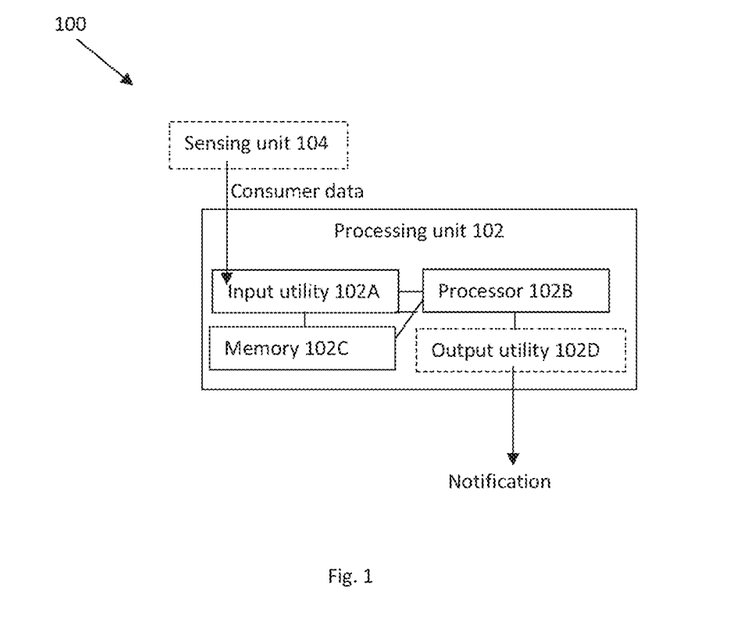
FIG. 1 is a schematic block diagram illustrating the main functional parts of the system of the present invention according to one aspect of the invention.

Reference is made to FIG. 1 showing a block diagram representing the main functional parts of the system 100 being configured for alerting on detection of a consumer with a vision impairment. System 100 can be placed in any store. For example, a preferred location can be next to best-selling products, or popular locations in the store. System 100 comprises a processing unit 102 being configured and operable for receiving input scene data (from any data source) being indicative of a scene of at least one consumer in a certain environment, identifying in the scene data a certain consumer and its related consumer condition, identifying an event being indicative of a behavioral compensation for vision impairment, and, upon identification of such event, sending a notification relating to the vision impairment. The notification can include the identified event and/or consumer data indicative of the identified consumer (e.g. an image of the consumer that triggered the event, or an image in which the consumer's face is in clear view), and/or ophthalmologic recommendations based on the identified event, and/or an appointment for a vision test. The ophthalmologic recommendations may relate to any optical information comprising at least one lens options recommendations such as progressives (e.g. specific progressive lens designs) bifocals, trifocals. The ophthalmologic recommendations may also relate to the use of type of lens design such as sport (in case of curved frame), as worn (in case of abnormal posture of wear), or even short corridor one (in case of "good" Rx but still chin lifting). More specifically, the ophthalmic recommendations can also be aimed at increasing the sell of some products such as thinner lenses, eyewear for sport, bifocal trade for multifocal, computer/relax for near tasks etc.

However, it should be noted that the notification relating to the vision impairment may also include the lack of an identified event, indicating that the consumer does not have any vision impairment. The notification is then a positive notification, indicating that there is no vision impairment, and there is no need for new glasses. In some cases, the seller receives the notification, and reacts accordingly, and, in other cases, the consumer merely receives the notification.

Processing unit 102 comprises a computer system comprising a data processor and being a part of and connected to a computer network. Processing unit 102 may comprise a general-purpose computer processor, which is programmed in software to carry out the functions described herein below. Unless specifically stated otherwise, as apparent from the following discussions, it is appreciated that throughout the specification discussions utilizing terms such as "identifying", "determining", "comparing", "calculating", "processing" or the like, refer to the action and/or processes of a computer that manipulate and/or transform data into other data. Also, operations in accordance with the teachings herein may be performed by a computer specially constructed for the desired purposes or by a general-purpose computer specially configured for the desired purpose by a computer program stored in a computer readable storage medium. Processing unit 102 comprises a processor 102B i.e. signal analyzer module configured and operable for identifying, from the signal data, a certain consumer and a consumer condition, and generating data indicative thereof, thereby enabling notifying a user (e.g. seller) of notification data. Processor 102B is capable of person identification and tagging. Processor 102B may also identify the presence of a frame to identify whether the consumer is wearing glasses or not, and enable to distinguish between cases in which the consumer is over/under corrected with their current eyewear (if any), whether the detected vision impairment is unrelated to their current eyewear (i.e. the patient is either uncorrected, or corrected with contact lenses). Processor 102B may also be configured and operable to identify eyelids, eyes and change in their shape and/or position. The processor may also be configured to identify the position and orientation of the head. The processing unit 102 may further comprise a communication interface utility configured and operable for data communication with a user's communication device via the computer network for communicating the notification data to the user's communication device. The network interface allows the processing unit 102 to communicate with an authentication server, a file storage server, an advertiser server, or a social media server if needed. The software may be downloaded to processor 102B in electronic form, over a network, for example, or it may alternatively be provided on tangible media, such as optical, magnetic, or electronic memory media. In a specific and non-limiting example, processing unit 102 is configured and operable to identify a consumer, identify in the image visual behavior (difficulties) or wrong eyewear usage behavior of the detected consumer (if the consumer is wearing eyewear), and send an alert to retail stores to approach the consumer in order to recommend a vision test, or to renew their prescription, or to alert the consumer, advising him to take a vision test. The system may also recommend a lens design better suited for the user, addressing the wrong eyewear usage identified (if any). The specific lens designs recommendation may be made based on the frame worn by the consumer. For example, a design optimized for 'wrap' frames if the frame worn has a large panoramic tilt, or a short corridor design if the consumer's Rx is correct, but the consumer is lifting his/her chin.

Different events may be identified simultaneously or sequentially. Processing unit 102 may run a series of different algorithms to identify different events relating for example to the position and orientation of the head. In a specific and non-limiting example, the position and orientation of the head may include squinting, chin lifting, increase or decrease of viewing distance between the consumer and an object being observed, or changing the position of the eyeglasses on the consumer's face. The event may be identified by identifying images having an image feature being indicative of behavioral compensation, performing a Bruckner test, performing a Hirschberg test, and measuring the blink count/frequency. Identifying the event may comprise identifying images having an image feature being indicative of behavioral compensation, performing a Bruckner test, performing a Hirschberg test, and measuring the blink count/frequency for a certain period of time.

For example, processing unit 102 may process the received data to identify a squinting event. Squinting can indicate visual defects, e.g. low visual acuity. It should be noted that squinting narrows the pupil entrance, enhances pinhole effect, and reduces distortions. Squinting can be detected using known algorithms based on computer vision/deep learning by using facial feature tracking, or by comparison to a reference data. The percentage of the pupil region blocked by eyelids may be measured, and the degree of squinting can be determined by calculating the degree to which the eye is closed/open. If a squinting event is detected, the notification data relating to the vision impairment comprises recommendations for corrective eyewear, or a different prescription to what the consumer is wearing.

Additionally or alternatively, processing unit 102 may process the received data to identify a chin lifting event. Chin lifting can be detected by using head tilt angles within a pre-defined range as can be extracted from known face tracking/head orientation algorithms that output the "pitch" of the head by calculating distance between facial features. Chin lifting can indicate that the consumer has difficulty locating the near segment in their current (progressive) eyewear, and the position of the near segment may not be optimal (also similar to squinting). If a chin lifting event is detected, the notification data comprises recommendations for progressive eyewear, or a different prescription to what the consumer is wearing.

Additionally or alternatively, processing unit 102 may process the received data to identify an event being related to an abnormal distance between the item and the consumer's face. Processing unit 102 may measure the distance between the item and the consumer's face. The measured distance may then be compared to a reference data (e.g. default value) containing a distance threshold defining abnormality. For example, the consumer may bring item(s) closer in order to clearly see small figures. Processing unit 102 may analyze the item held by the consumer to identify the size of the contents therein. If a consumer adjusts the distance between his eyes and an item to very small distances in order to see small figures, the notification data comprises recommendations for a new prescription. The distance between the consumer and viewed object can also be measured using any proximity sensor.

Additionally or alternatively, processing unit 102 may process the received data to identify an event being related to the change of the distance between an object and a consumer's face/eyes. The event comprises a change in the distance between the object and the consumer's face/eyes. Processing unit 102 may detect a change in the distance between the object and the consumer's face/eyes. For example, a consumer may move an item farther away from or closer to his face/eyes in order to focus. If a consumer adjusts the distance between his eyes and an item to view at greater distances, the notification data comprises recommendations for a new prescription which may comprise recommendations for progressive addition lenses (PAL), and/or recommendations for a higher additional power (ADD portion) if the consumer is a progressive/bi-focal wearer.

Additionally or alternatively, processing unit 102 may process the received data to identify an event being related to the change of the position of the eyeglasses worn by the consumer. For example, lifting eyeglasses, sliding the glasses on the nose, or lowering eyewear, may be identified. Processing unit 102 may detect the change of the position of the eyeglasses on the consumer's face by running an algorithm detecting images in which the consumer is reading with lifted eyewear while reading. For example, pupil/eye can be identified in the image outside the frame (depending on the perspective of the camera). If the consumer lifts his eyewear in order to view small figures, i.e. text at reading distance, the notification data comprises recommendations for a new prescription which may comprise recommendations to test for myopia, and his prescription (including any addition) should be reviewed.

Additionally or alternatively, processing unit 102 may process the received data to identify an event being related to the change of the position of the eyeglasses worn by the consumer and consumer observation through lenses. If the distance between lenses and eyes increases, the notification data comprises recommendations for a new prescription which may comprise recommendations for more additions.

Additionally or alternatively, processing unit 102 may process the received data to run a Bruckner Test. A Bruckner Test may be run on at least one image. The brightness difference of the pupils is evaluated. The crescent predicts hyperopia and myopia. Its size predicts the amount, and its location predicts the type of visual defect.

Additionally or alternatively, processing unit 102 may process the received data to compare the differences in light intensity between the two eyes to identify amblyopia or anisometropia.

Additionally or alternatively, processing unit 102 may process the received data to run a Hirschberg test to detect strabismus.

Additionally or alternatively, processing unit 102 may process the received data to measure the blink count/frequency for a certain period of time. For example, the period of time may be 15 seconds.

Additionally or alternatively, processing unit 102 may process the received data to identify a visible strabismus.

Additionally or alternatively, processing unit 102 may process the received data to identify a nystagmus.

Additionally or alternatively, processing unit 102 may process the received data to identify white return defining a cataract or a Retinoblastoma.

In some embodiments, system 100 comprises at least one sensing unit 104 configured and operable for detecting the scene data of at least one consumer being in a certain environment. Sensing unit 104 may comprise at least one camera recording at least one image of at least one consumer and/or motion detector(s) and/or eye trackers, for example, an eye tracker device with at least one infrared camera and at least one infrared illuminating element. In a specific and non-limiting example, sensing unit 104 may be placed in a housing of an eyewear frame digital or optical display. However, the location of sensing unit 104 is not limited to any location and can be accommodated at in other suitable places (in a consumer personal device for example). For example, a plurality of cameras can be located at various heights in order to obtain images from an optimal perspective. The camera may be an HD camera associated with an eye tracker. In addition to the sensing data acquired by the sensing unit 104, the input data may also comprise location and orientation of the sensors, the store configuration relative to these sensors, i.e. where each aisle is, what products are displayed in each aisle, and how it is positioned (e.g. on shelves, wall mounted, mirrors, etc.). The sensing unit 104 can be located, for example, within a mirror mounted on a wall, within a shelf displaying merchandise, above a poster or product, or mounted on the ceiling with a relevant angle. Existing surveillance cameras can be used as part of the sensing unit 104. The sensing data can be an image/video data of the consumer and of the consumer's condition. The consumer's condition may comprise consumer's face and/or posture and/or position. Other sensors can also be used, additionally or alternatively, to detect sound or motion to determine the consumer's position and location relative to the consumer's environment (e.g. to specific reference objects in the environment). A combination of data from several sensors can be used to determine the consumer's condition (e.g. consumer's position, posture, and location relative to the consumer's environment). The cameras can be permanently positioned, or can be moved from position to position, depending on the store layout. The camera location can be determined based on a location device mounted on the camera or based on its position captured by one of the other cameras.

In some embodiments, processing unit 102 comprises an input interface/communication interface utility/data input utility 102A including a communication module configured for data communication, via the network, with at least one data source (e.g. sensing unit 104) providing signal data, and a data processor 102B adapted for analyzing the signal data, and generating output data via an optional data output utility 102D comprising notification data describing the vision impairment. The notification data may be sent immediately upon identifying a vision impairment, or when instructed by the user. It should be understood that the signal data, or at least part thereof, may be provided directly from the sensing unit 104 and/or from personal communication devices. Processor 102B may transmit data regarding the behavioral compensation for vision impairment via the data output utility 102D, via a data communication (e.g. via cellular network) to a communication module of a central computer. Data input utility 102A is configured and operable for receiving at least one signal data via the computer network. Data input utility 102A may typically be located in the vicinity of the sensing unit 104, and communication between them may be a short-range communication via Bluetooth, be Wi-Fi based, or via other communication methods.

In some embodiments, data output utility 102D comprises an external transceiver including a communication interface utility for receiving the output data from the processor 102B and at least one of displaying the notification data or data communication on a user's communication device. Communication interface utility may be configured and operable for data communication with a user's communication device via the computer network for communicating the notification data to the user's communication device. For example, together with the notification data, the transceiver or the user's communication device may display to the user notification data and/or instructional data.

In some embodiments, the processing unit 102 may query/cross-reference the received data with data in a database to generate notification data, and may communicate such notification data to a display device at which the processing unit may signal to display a message corresponding to the notification data. Processing unit 102 may comprise a memory 102C (i.e. non-volatile computer readable medium) for storing a database e.g. reference data indicative of behavioral compensation for low visual acuity and/or data indicative of the notification and/or data indicative of a follow-up of the notification. Memory 102C may be relayed via wireless or wired connection by a unit external to a central database. Processor 102B may record the received data in database in memory 102C and/or may query/cross-reference the received data with data in the database to identify if the data is indicative of behavioral compensation for low visual acuity and may communicate such data to a device (e.g. display or mobile device) at which processor 102B may signal to display a message corresponding to the identified data. To this end, the preselected data stored in a database may be used to compare at least one image of the sensing data with images being indicative of a plurality of behavioral compensation for low visual acuity stored in the database. For example, as will be described below, the reading distance of a consumer may be identified by storing in a database, before identification of an event being indicative of a behavioral compensation for low visual acuity, a plurality of reading distances being indicative of vision impairment.

Data processor 102B is adapted for identifying which of the sensing data is indicative of a behavioral compensation for low visual acuity, and which is not. The database may be implemented with Microsoft Access, Oracle, or other suitable commercial database systems. In some embodiments the system 100 is configured in a cloud-based configuration and/or utilizes Internet-based computing, so that parts of processor 102B, and/or memory 102C may reside in multiple distinct geographic locations. In some embodiments, storage may be separate from the server(s) (e.g. SAN storage). If separate, the location(s) of the storage may be in one physical location, or in multiple locations and connected through any type of wired or wireless communication infrastructure. The database may rely on any kind of methodology or platform for storing digital data. The database may include for example, traditional SQL databases such as Oracle and MS SQL Server, file systems, Big Data, NoSQL, in-memory database appliances, parallel computing (e.g. Hadoop clusters), etc. Memory 102C, being configured as the storage medium of the database, may include any standard or proprietary storage medium, such as magnetic disks or tape, optical storage, semiconductor storage, etc. The database may also store data relating to a specific consumer for other purposes.

Figure 2A:
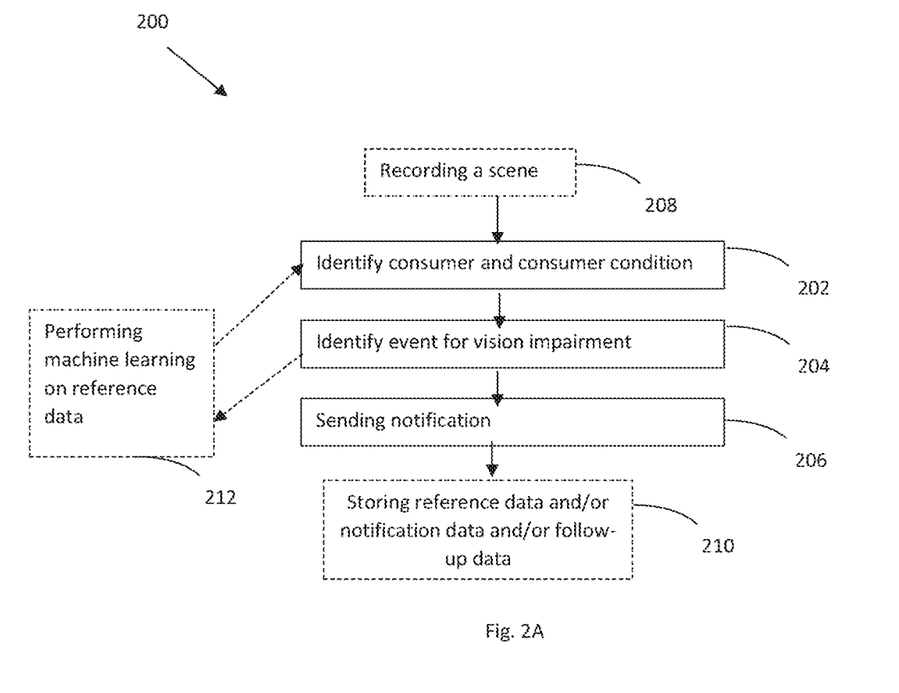
FIG. 2A is a schematic flow chart illustrating the main computer-implemented steps of the method of the present invention according to one aspect of the invention.

Reference is made to FIG. 2A showing a schematic flow chart representing the main steps of the method 200 of the present invention. Method 200 comprises identifying in 202 captured data indicative of a scene of at least one consumer being in a certain environment, a certain consumer (i.e. specific individual) and the related consumer condition (i.e. his visual behavior). The analysis comprises comparisons between captured data and reference data. Reference data can be data obtained in conjunction with the captured data (i.e. data captured in two states). Additionally or alternatively, as shown in 212, reference data can be based on machine learned/statistically shown correlations for defaults of measured values. As will be described further below, the method may comprise, after having identified an event for vision impairment in 204, performing a machine learning procedure in 212 in which the identified event is stored as a reference data to be correlated with future measured data. The reference data can also be personal. The technique is configured to identify the certain consumer (e.g. "a repeat customer") and compare the changes in his visual behavior. The customer may be identified by using any known face recognition algorithm or by using a mobile identification number. If an event for vision impairment is detected in 204 e.g. his visual behavior is indicative of visual difficulties and/or wrong eyewear usage in behavior, or that no abnormalities were detected, a notification is sent to the relevant party (e.g. retailers, retail salesperson, optometrist, customer, etc.) in 206 to approach the consumer in order to recommend a vision test, or to renew their prescription. The relevant party can be a third party being located at a different location. For example, the event may be triggered in a large chain store, and the notification may be sent to local optometrists that subscribe to the alert. The notification can be sent to one or more parties that can be predefined in the system or selected according to shifts of employees defined in the system. The notification can be sent in the form of an email, text message, audio message, etc. The notification may include an appointment for a vision test. For example, the method may comprise automatically scheduling an eye examination, if an interface with the scheduling is available. The booked appointment can be confirmed once the consumer is notified and approves the time. The notification can include the identified event and/or data indicative of the identified consumer (e.g. an image of the consumer that triggered the event). The notification can also include ophthalmologic recommendations based on the identified event(s) such as instructions regarding the probable vision requirements of the consumer. The notification can also include a recommendation to take a visual test or get new glasses.

In some embodiments, method 200 comprises storing reference data and/or notification data and/or follow-up data in 210. As described above, all the data may be saved into a database. The data gathered can be continually monitored and the detection algorithms can also be improved. The saved notification data can include the event and/or metadata regarding the image (time of day, location, age, gender, etc.), to where the alert was sent, etc. The saved data may also include follow-up data to enable possible tracking of the outcome of the notification, such as details with respect to a potential sale, a false identification, or an eye examination prescription (Rx) result. After the eye examination, the Rx parameters (e.g. Sph, Cyl, Axis, Add Power) or Visual Acuity (VA) can be stored and related to the detected event. If the consumer accepts the terms, the consumer's personal data can also be stored with the notification data.

A wide Cloud/Big Data service may be provided that gathers data from the sensing unit and uses analytics software to map, alert, and generate reports based on readings collected by the devices. The system and method according to any of the preceding embodiments may include a cloud service that gathers data from devices of the sensing unit and uses big data analytics to analyze readings collected by the devices. Big data analytics can then be used to identify new correlations from cross referenced data. The server application typically includes a big data analytics engine which processes collected data (raw data and meta-data) and generates various views (reports). The collected data may be stored in a database which may be indexed per source (front end), time stamp and/or geographical location. The analytics engine, which may employ conventional big data algorithms for management, storage, SLA and presentation, may handle huge data structures and may generate a specific view that compacts and focuses that data.

As shown in 212, the method may comprise employing algorithms of machine learning which are trained using training data sets that include large number of consumers who were detected and identified as having visual defects. The database may be determined by various machine learning techniques utilizing analytical data. The correlation may be determined employing machine learning techniques in order to establish a precise correlation and weighting function. Once a sufficient sample set providing sensing data and image analysis data is obtained and correlated with the analysis of the method of the present invention, this can be used to construct a database to be used by machine learning programs to generate a weighting function. Machine learning and pattern recognition can be viewed as two facets of the same field. When employed in industrial contexts, machine learning methods may be referred to as predictive analytics or predictive modeling. There are many software tools which are used as machine learning tools including, for example, the following tools: dlib, ELKI, Encog, H20, Mahout, mlpy, MLPACK, MOA (Massive Online Analysis), ND4J with Deeplearning4j, NuPIC, OpenCV, OpenNN, Orange, PyMC, R, scikit-learn, scikit-image, Shogun, Torch (machine learning), Spark, Yooreeka, Weka, KNIME, RapidMiner, Amazon Machine Learning, Angoss Knowledge STUDIO, Databricks, IBM SPSS Modeler, KXEN Modeler, LION solver, Mathematica, MATLAB, Microsoft Azure Machine Learning, Neural Designer, NeuroSolutions, Oracle Data Mining, RCASE, SAS Enterprise Miner, STATISTICA Data Mine, and TensorFlow.

Additionally or alternatively, Artificial Intelligence (AI) techniques may be used to detect alternate behavior or events indicative of vision impairment.

In some embodiments, method 200 comprises recording a scene in 208 (e.g. continuously). Recording a scene in 208 comprises detecting a consumer in the specific environment.

Figure 2B:
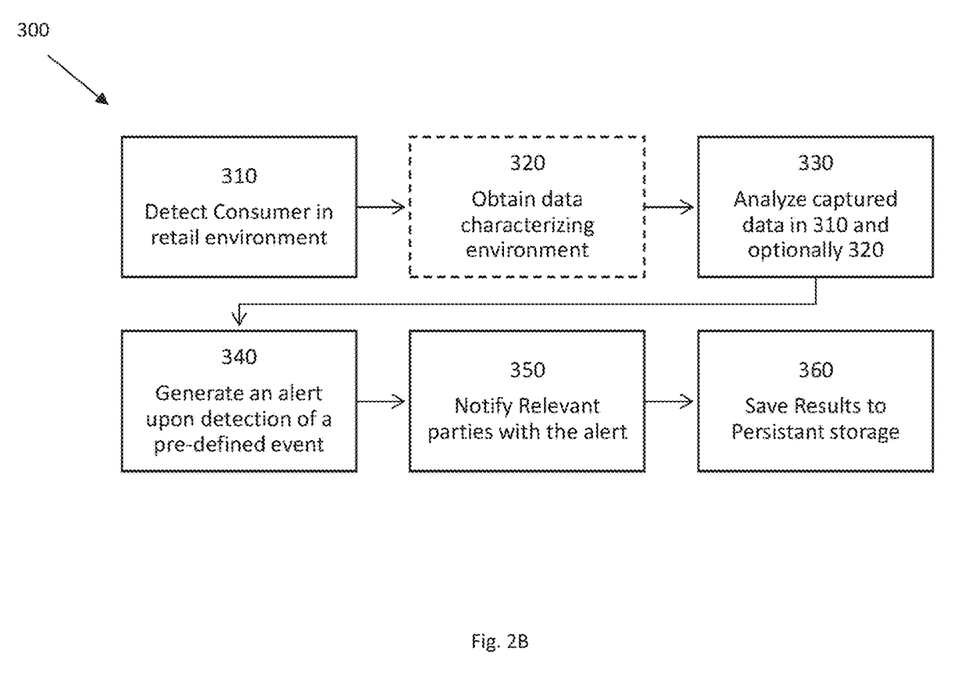
FIG. 2B is a schematic flow chart illustrating a specific and non-limiting example of the method of the present invention according to an embodiment of the invention.

Reference is made to FIG. 2B showing a schematic flow chart illustrating a specific and non-limiting example of method 300 of the present invention. Method 300 comprises, as described above, detecting a consumer in a certain environment in 310. Step 320 is an optional step that involves obtaining data characterizing the environment. For example, if one camera is located on a display and captures image data of a consumer's face/profile, and another camera captures the scene from a distance in which the object of interest to the consumer is contained, the position of the relevant objects in the environment relative to the consumer can be determined. Alternatively, the environment can be mapped in a virtual model, and updated as necessary, and the position of the object of interest to the consumer relative to the consumer can be determined by the location of the consumer in the virtual 3D model. The data obtained in step 310 and optionally 320 is received and analyzed in 330 in order to determine an event being indicative of a behavioral compensation for vision impairment (e.g. at least one parameter that aids in prescribing eyewear). If an event (from the pre-defined possible events) is detected, an alert can be generated in 340 and sent to the relevant party in 350. The notification data is then saved to a database in 360.

EXAMPLES

Various examples were carried out to prove the embodiments claimed in the present invention. Some of these experiments are referred to hereinafter.

Example 1: A consumer approaches a display, lifts a product, and then raises his glasses in order to read the product label. The event of changing the position of the eyeglasses worn by the consumer is detected, which triggers a multimedia message to be sent to the salesperson on duty in the store. The message includes instructions to update the consumer that he is likely myopic (or presbyopic if the consumer's age is likely over 40 years), an explanation of the rationale, and recommendation of an eye examination for the precise prescription. The system can book an appointment for an eye examination, and the message can include the scheduled time for the examination. The message can also include an image of the consumer that triggered the event and can also include the consumer's location in the store/venue.

Example 2: A consumer approaches a display, lifts a product, and then raises his glasses in order to read the product label. The event of changing the position of the eyeglasses worn by the consumer is detected, which triggers a voice message to be broadcasted either directly to the consumer, or sent to the consumer's device (by Bluetooth, etc.). The message includes the probable vision problem, and a possible appointment for a vision evaluation. The consumer can then approve the appointment and undergo an eye examination.

Example 3: A consumer looks at an advertisement and tries to read from a 2-3-meter distance. The event of changing the orientation of his face and/or squinting is detected, which triggers a text message to be broadcasted either directly to the consumer, or sent to the consumer's device (by Bluetooth, etc.). The message includes the probable vision problem, and a possible appointment for a vision evaluation. The consumer can then approve the appointment and undergo an eye examination.

Example 4: A consumer uses his mobile phone and needs to bring the device closer or farther. The event of changing the viewing distance between the consumer and his mobile phone is detected, which triggers a text message to be broadcasted either directly to the consumer, or sent to the consumer's device (by Bluetooth, etc.). The message includes the probable vision problem, and a possible appointment for a vision evaluation. The consumer can then approve the appointment and undergo an eye examination.

A wide variety of frames are available to consumers when they shop for eyewear, including geometrical parameters of the lens and the frame, and in addition, frames can be rimmed/rimless/half-rimmed, and are formed from a variety of materials (e.g. plastic, metal, ceramic, nylon, wood, etc.), and frame can have varying geometries (e.g. thickness, etc.) Certain frames are better suited to house lenses with different prescriptions. For example, lenses for myopes have thick edges, and are less aesthetic when mounted in large frames, and when mounted in rimless or half rimmed frames, as the edges are more apparent. To assist the consumer in selecting a frame corresponding to a multiplicity of criteria, in some embodiments, the processing unit is configured for providing a frame recommendation. The frame recommendation may comprise at least one spectacle frame parameters such as frame shape (i.e. lens contour), a frame thickness dimension or a frame color/texture. The frame recommendation may be based on at least one of the followings: ophthalmic recommendations (either stored from previous measurements, or detected from events); facial features (e.g. pupillary distance, nose shape, eye shape, face contour shape, skin tone, eye color, canthus length) or previous eyewear preferences (either stored from previous measurements, or detected from current images).

The system's memory is then configured for storing a database including a multiplicity of data sets related to a plurality of spectacle frame parameters including different models (e.g. frame shape, material and style) and sizes. The frame recommendation may thus be based on the correlation between different frames parameters and different prescriptions.

Certain frame shapes are better suited to consumers with specific facial features. In one embodiment, frame selection may also be done by using a facial shape/structure recognition tool included in the computer platform. Such a tool can be configured to detect the user's facial shape and structure and make recommendations for the most appropriate frame shape, size, material and style. Such a tool can also be configured to recognize skin tone information which may be used to make frame color recommendations. The frame recommendation may thus be based on the correlation between different frames parameters and facial features.

Additionally, the consumer may have an affinity for a specific frame type based on their current eyewear (if relevant), e.g. if the consumer is wearing eyewear that having a special shape (e.g. "wrap" with a high panoramic angle), he may prefer frames with this feature in the future. The frame recommendation may thus be based on the correlation between different frames parameters and parameters and eyewear preferences.

The previous eyewear data information can also be used to generate an additional ophthalmic recommendation, e.g. if wrap lenses are detected, an optical design to correct for distortions generated by the wrap can be recommended. In some embodiments, if a high prescription is detected in an event (i.e. hyperope or myope), a recommendation for a high-index lens can be made.

The following table 1 provides two non-limiting examples of detected event, age, facial features and the determined recommended frame, contour and ophthalmic recommendation.

TABLE 1

| Event Detected | Age | Facial Features | Recommended Frame | Recommended contour | Ophthalmic Recommendation |
|---|---|---|---|---|---|
| Myope - | 20- | Wide- | Full rimmed, | According | High-index |

TABLE 1-continued

| Event Detected | Age | Facial Features | Recommended Frame | Recommended contour | Ophthalmic Recommendation |
|---|---|---|---|---|---|
| high | 25 | set eyes, round face | and relatively thick frame | to facial optimization | lenses, single vision minus prescription |
| Hyperope - med | 50-55 | Wide nose, long face | any frame thickness, any rimming, no nose pads | B - high (long frame) | Progressive lenses, Mid-high index lenses |

The invention claimed is:

1. A system for alerting on vision impairment, said system comprising a server connectable, via a communication network, to subscribers' computer entities comprising medical clinics and stores communication devices and user's communication devices, the server comprising:
   a communication interface utility configured and operable for data communication with the user's communication devices for communicating request and notification data, and with said medical clinics and stores communication devices; and
   a processing unit configured and operable for:
      upon identifying a consumer in the medical clinic or store, via the user's communication device of the consumer, and obtaining consumer's permission, initiating passive observation of the consumer within the medical clinic or store, said passive observation comprising:
      receiving, from at least one sensing unit in said medical clinic or store, a scene data;
      processing the scene data to identify the consumer in environment of the medical clinic or store and determine a condition of the consumer with respect to at least one object of consumer's interest in the environment of the medical clinic or store being indicative of visual behavior of the consumer;
      analyzing the scene data and the condition of the consumer with respect to the at least one object of consumer's interest to identify an event being indicative of an unconscious behavioral compensation for vision impairment of said consumer, by carrying out at least one of: identifying the event upon comparison between the scene data and reference data; or determining a probability for a vision impairment of the consumer based on comparison between the scene data and reference data; and
      upon identification of the event, operating the communication interface utility to send a notification, relating to the vision impairment, to at least one of said user's communication device of the consumer, and said medical clinics and stores communication devices.

2. The system of claim 1, wherein said at least one sensing unit comprises at least one of:
   at least one imaging unit configured and operable for capturing at least one image of at least a portion of the consumer's head;
   at least one motion detector configured and operable for detecting consumer data being indicative of a motion of the consumer; or
   at least one eye tracker configured and operable for tracking eye motion of the consumer.

3. The system of claim 2, wherein the at least one imaging unit comprises a plurality of cameras placed at different heights.

4. The system of claim 1, wherein said processing unit is configured and operable for at least one of:
   identifying the consumer's condition with respect to the at least one object of consumer's interest, wherein said consumer's condition comprises a consumer data being indicative of the consumer's position and location relative to at least one object of the consumer's interest in the environment of the medical clinic or store; wherein said consumer data comprises at least one of the consumer's face, eyewear, posture, position, sound or motion; or
   providing a frame recommendation being based on at least one of (i) ophthalmic recommendations; (ii) facial features; (iii) previous eyewear preferences; or (iv) a correlation between different frames parameters and different prescriptions.

5. The system of claim 1, wherein said processing unit comprises at least one of;
   a memory for storing at least one of a reference data indicative of behavioral compensation for vision impairment, data indicative of the notification, or data indicative of a follow-up of the notification; and
   a communication interface being configured for sending the notification to at least one of the identified consumer or a third party.

6. The system of claim 5, wherein said memory is configured for storing a database including a multiplicity of data sets related to a plurality of spectacle frame models and sizes.

7. The system of claim 1, wherein said network is configured to receive and respond to requests sent across the network; transmitting one or more modules of computer executable program instructions and displayable data to the network connected user computer platform in response to a request, wherein said modules include modules configured to: receive and transmit image information, transmitting a frame recommendation and an optical lens option recommendation based on received image information, for display by the network connected user computer platform.

8. The system of claim 1, wherein said analyzing of the scene data and the condition of the consumer with respect to the at least one object of consumer's interest to identify the event comprises identifying an image feature indicative of behavioral compensation, said image feature comprising one or more of the following: squinting, head orientation, certain distances between the object of the consumer's interest and the consumer's eyes, certain position of eyeglasses on the consumer's face, strabismus, cataracts, and reflections from the eye.

9. The system for alerting on vision impairment of claim 1, wherein said event comprises at least one of (i) a particular position and orientation of the customer's head, (ii) an increase or a decrease of a viewing distance between the consumer and a viewed object, and (iii) changing the position of an eyeglasses worn by the consumer.

10. A non-transitory computer readable storage medium that, when executed by a processing unit, causes the processing unit to:
   in response to data indicative of a consumer in environment of subscriber medical clinic or store, communicate with the consumer via user communication device of the consumer to obtain consumer's permission for passive observation of the consumer within said environment of the medical clinic or store;

in response to the consumer's permission, communicate with computer entities of the subscriber medical clinic or store to initiate said passive observation of the consumer within the medical clinic or store;

in response to data being indicative of the passive observation of the consumer in said environment, analyze said data to:

generate data indicative of a condition of the consumer with respect to at least one object of consumer's interest in the environment of the medical clinic or store being indicative of visual behavior of the consumer;

identify in the data indicative of the visual behavior of the consumer, an event being indicative of an unconscious behavioral compensation for vision impairment of the consumer; and upon identification of the event, send a notification relating to the vision impairment.

11. The non-transitory computer readable storage medium of claim 10, wherein said event comprises at least one of (i) a particular position and orientation of the customer's head, (ii) an increase or a decrease of a viewing distance between the consumer and a viewed object, and (iii) changing the position of an eyeglasses worn by the consumer.

12. A computer platform for facilitating eye-glasses marketing or selection, comprising:

a camera configured and operable to collect a scene data being indicative of a passive observation of at least one consumer with respect to objects of consumer's interest in an environment of a medical clinic or store;

a processor configured to execute computer program instructions to: cause the processor to instruct the camera to collect an image being indicative of the scene data, identify in the image a specific consumer, being the consumer who has provided a permission for the passive observation thereof in said environment; analyze the data indicative of the passive observation of the specific consumer to determine a condition of the specific consumer with respect to at least one object of interest within said environment being indicative of visual behavior of the specific consumer; identify, from data indicative of the visual behavior of the specific consumer, an event being indicative of an unconscious behavioral compensation for vision impairment of the specific consumer; and, upon identification of such an event, send a notification relating to the vision impairment;

a local storage for the processor executable instructions for carrying out storage of information.

13. The method computer platform for facilitating eyeglasses marketing or selection of claim 12, wherein said event comprises at least one of (i) a particular position and orientation of the customer's head, (ii) an increase or a decrease of a viewing distance between the consumer and a viewed object, and (iii) changing the position of an eyeglasses worn by the consumer.

* * * * *